(12) United States Patent  
Kobayashi

(10) Patent No.: US 7,411,177 B2  
(45) Date of Patent: Aug. 12, 2008

(54) MULTI-SPECTRUM IMAGE CAPTURING DEVICE AND MULTI-SPECTRUM ILLUMINATING DEVICE

(75) Inventor: Hiroyoshi Kobayashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/669,779

(22) Filed: Jan. 31, 2007

(65) Prior Publication Data

US 2007/0120046 A1  May 31, 2007

Related U.S. Application Data

(60) Division of application No. 11/418,348, filed on May 4, 2006, which is a continuation of application No. PCT/JP2004/016662, filed on Nov. 10, 2004.

(30) Foreign Application Priority Data

Nov. 14, 2003  (JP)  ............................. 2003-385540

(51) Int. Cl.
 *G02B 6/06* (2006.01)
 *G01N 21/25* (2006.01)
 *G01J 3/46* (2006.01)
(52) U.S. Cl. .............................. 250/227.2; 250/227.23; 356/402; 356/420
(58) Field of Classification Search ................. 356/402, 356/420; 250/227.2, 227.23
See application file for complete search history.

(56) References Cited

U.S. PATENT DOCUMENTS

| | | | | |
|---|---|---|---|---|
| 4,033,698 A | * | 7/1977 | Demsky et al. | ............. 356/402 |
| 5,229,841 A | * | 7/1993 | Taranowski et al. | ......... 356/406 |
| 6,147,761 A | | 11/2000 | Walowit et al. | |
| 6,847,447 B2 | | 1/2005 | Ozanich | |
| 2001/0052977 A1 | * | 12/2001 | Toyooka | ..................... 356/326 |
| 2003/0076499 A1 | * | 4/2003 | Yamada et al. | .............. 356/419 |

FOREIGN PATENT DOCUMENTS

| | | |
|---|---|---|
| EP | 0 522 548 A1 | 1/1993 |
| JP | 5-187919 A | 7/1993 |
| JP | 7-296615 A | 11/1995 |
| JP | 8-247929 A | 9/1996 |
| JP | 09034371 A  * | 2/1997 |

(Continued)

*Primary Examiner*—Thanh X. Luu  
*Assistant Examiner*—Brian J Livedalen  
(74) *Attorney, Agent, or Firm*—Frishauf, Holtz, Goodman & Chick, PC

(57) ABSTRACT

A multi-spectrum image capturing device includes a multi-spectrum illuminating device comprising LED's for emitting lights of different wavelengths from one another, a plurality of optical rods for relaying the lights emitted from the LED's, an optical diffusion element for diffusively reflecting the lights from the optical rods by a white diffusion surface and an aluminum-coated reflecting surface to be irradiated at an angle of about 60° with respect to an image-capturing optical axis, and an optical sheet for further diffusing the lights from the optical diffusion element, and also includes an image-capturing optical system and a CCD for forming an image based on lights reflected from an irradiated surface under illumination by the multi-spectrum illuminating device to capture the formed image. An image output captured by the CCD is analyzed to measure color components of the irradiated surface.

8 Claims, 11 Drawing Sheets

FOREIGN PATENT DOCUMENTS

| | | |
|---|---|---|
| JP | 9-218356 A | 8/1997 |
| JP | 9-270885 A | 10/1997 |
| JP | 10-132663 A | 5/1998 |
| JP | 10-134621 A | 5/1998 |
| JP | 11-218447 B2 | 8/1999 |
| JP | 11-305141 A | 11/1999 |
| JP | 2002-345760 A | 12/2002 |
| JP | 2003-153041 A | 5/2003 |

\* cited by examiner

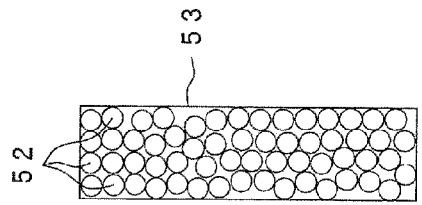
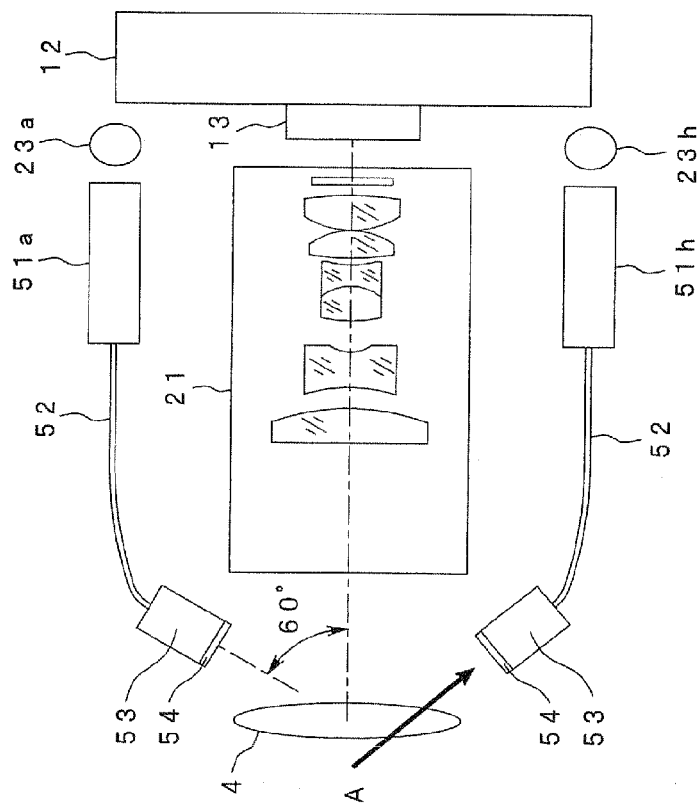
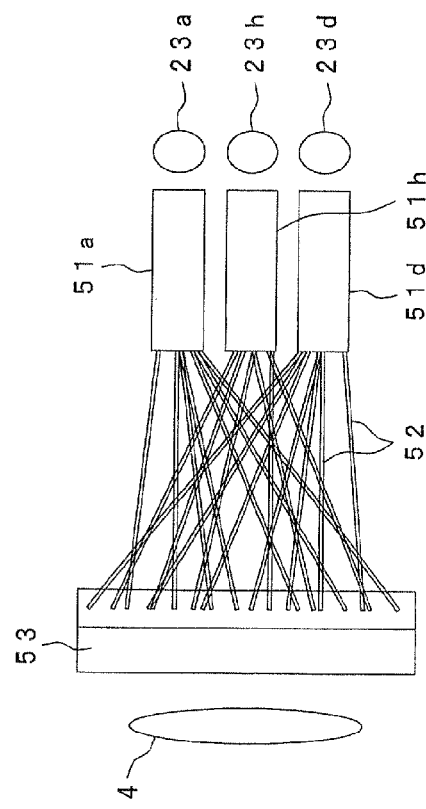

MULTI-SPECTRUM IMAGE CAPTURING DEVICE AND MULTI-SPECTRUM ILLUMINATING DEVICE

CROSS REFERENCE TO RELATED APPLICATION

The present application is a Divisional application of U.S. application Ser. No. 11/418,348 filed May 4, 2006, which is a continuation application of PCT/JP2004/016662 filed on Nov. 10, 2004 and claims the benefit of Japanese Application No. 2003-385540 filed in Japan on Nov. 14, 2003, the entire contents of which are incorporated herein by reference.

BACKGROUND OF THE INVENTION

1. Field of the Invention

The present invention relates to a multi-spectrum image capturing device and a multi-spectrum illuminating device which are used to irradiate lights of different wavelengths for measurement of color components.

2. Description of the Related Art

Various types of illumination devices for illuminating a target to observe the targeted object surface and the like or capture its image for analysis have been proposed so far.

For example, Japanese Unexamined Patent Application Publication No. 9-218356 discloses an optical device and an illumination head in which, for the purpose of observing the surface of a target similar to a mirror surface, an illumination light introduced by first light guide means is irradiated to the target from a position close to a shooting optical axis through second light guide means having a plurality of reflecting surfaces so that the target can be observed with bright light obtained by the regular reflection light.

Also, Japanese Unexamined Patent Application Publication No. 9-270885 discloses a technique using a ring-shaped light source in an illumination optical system assembled in a calorimeter, etc. A light emitted from the ring-shaped light source is reflected by a first conical mirror surface and is further reflected by a second concave mirror surface for irradiating a target.

Bulb lamps have hitherto been widely used as light sources for such illumination purposes. Recently, light emitting diodes (LED's) have also been used gradually increasingly in some fields. The LED is superior to the bulb lamp in points of lower power consumption and longer life. Further, the LED has advantageous characteristics such as emission in a narrower wavelength band and high color reproducibility.

As one of techniques recently developed by utilizing those advantages and characteristics of the LED, there is a technique for measuring a target color.

For example, Japanese Patent No. 3218601 discloses a device in which LED lights of three primary colors are sequentially emitted and directly irradiated to an irradiated surface such that the respective colors are overlapped with each other in a central area, and the lights reflected from the irradiated surface are received by a photodiode, for example, to determine a calorimetric value based on the intensity of each reflected light.

In the LED, the quantity of light emitted from one device is small. In trying to constitute an illuminator for use in colorimetry, the quantity of emitted light has to be increased, for example, by arraying a plurality of LED's. However, if a plurality of LED's are just simply arrayed for illumination, there is a possibility that the target is unevenly illuminated. Some solution is required to avoid such a possibility.

As one technique in consideration of that problem, Japanese Unexamined Patent Application Publication No. 10-134621, for example, discloses an illuminator for illuminating a semiconductor wafer, etc. for the purpose of inspection. When illumination lights are emitted from a plurality of LED's and transmitted through a fiber bundle, fibers constituting the bundle are arranged at random so that even illumination is performed.

From the viewpoint of exactly measuring the target color, it is also required to avoid the regular reflection light from being included in the reflected light to be received.

As one technique coping with that point, Japanese Unexamined Patent Application Publication No. 11-305141, for example, discloses a macrophotographic device and an optical device in which an annular light shield for shielding a regular reflection light is disposed between light guide means for irradiating an illumination light and a target to be illuminated.

In the calorimetric device disclosed in the above-cited Japanese Patent No. 3218601, because the lights of three primary colors are directly irradiated to the irradiated surface, whether unevenness in the quantity of light occurs in the irradiated surface is optically decided depending on the light distribution characteristic of each LED and the illumination distance. To obtain a quantity of the optically even illumination light, it is required to form a light beam which has high directivity regardless of the irradiation distance. It is however difficult to achieve that light distribution characteristic with only the LED. In this situation, an irradiated area where the lights emitted from the LED's corresponding to the three primary colors are overlapped with each other is obtained just in a small area, and the measurement can be performed just in such a limited small area. Further, according to the arrangement disclosed in the above-cited Japanese Patent, a target color cannot be always exactly measured because of a possibility that the regular reflection light from the irradiated surface enters the photodiode.

Also, the illuminator disclosed in the above-cited Japanese Unexamined Patent Application Publication No. 10-134621 is improved in point of performing even illumination through the fiber bundle as described above, but still have problems as follows. Because of substantially vertically directed illumination, the regular reflection light from the irradiated surface cannot be avoided from entering a CCD camera through a microscope, and exact color measurement cannot be realized. Further, the disclosed illuminator is intended to inspect a pattern on a semiconductor wafer, etc., and therefore it has no special arrangement for colorimetry. In other words, the disclosed illuminator does not have a structure adapted for a plurality of illumination lights of different wavelengths.

In the techniques disclosed in the above-cited Japanese Unexamined Patent Application Publications No. 9-218356, No. 9-270885 and No. 11-305141, the LED is not assumed to be as the light source. Therefore, those techniques include no contrivance to eliminate unevenness in the illumination which is caused in the case of using a plurality of LED's.

In view of the above-mentioned state of the art, an object of the present invention is to provide a multi-spectrum illuminating device and a multi-spectrum image capturing device which are able to perform illumination without causing unevenness in the quantity of light on an irradiated surface.

SUMMARY OF THE INVENTION

To achieve the above object, according to a first aspect of the present invention, there is provided a multi-spectrum image capturing device comprising a multi-spectrum illuminating device for irradiating lights of different wavelengths to an irradiated surface, and an image-capturing optical system for forming an image based on lights reflected from the irradiated surface under illumination by the multi-spectrum illuminating device, components of the reflected lights taken via the image-capturing optical system being analyzed to measure color components of the irradiated surface, wherein the multi-spectrum illuminating device comprises a plurality of light sources for emitting lights of different wavelengths from one another; optical rods for relaying the lights emitted from the light sources; and an optical diffusion element having a reflecting surface to reflect the lights from the optical rods, while diffusing the lights, such that the lights diffused by the reflecting surface are irradiated to the irradiated surface.

According to a second aspect of the present invention, in the multi-spectrum image capturing device according to the first aspect, the optical diffusion element includes an optical sheet for diffusing transmittal lights, the optical sheet being disposed in an optical path.

According to a third aspect of the present invention, in the multi-spectrum image capturing device according to the first aspect, the optical diffusion element includes an optical sheet having a gradation adapted to reduce unevenness in illumination on the irradiated surface, the optical sheet being disposed in an optical path.

According to a fourth aspect of the present invention, in the multi-spectrum image capturing device according to the first aspect, the optical diffusion element has a plurality of reflecting surfaces, and at least one of the plurality of reflecting surfaces is an aluminum-coated reflecting surface.

According to a fifth aspect of the present invention, in the multi-spectrum image capturing device according to the first aspect, the optical diffusion element has a plurality of reflecting surfaces, and at least one of the plurality of reflecting surfaces is a white-painted reflecting surface.

According to a sixth aspect of the present invention, in the multi-spectrum image capturing device according to the first aspect, the optical diffusion element has a narrowed portion formed such that a cross-sectional area substantially perpendicular to an optical path for transmission of the lights from the optical rods is smaller in an intermediate region of the optical path than in the entrance side and the exit side of the optical path.

According to a seventh aspect of the present invention, in the multi-spectrum image capturing device according to the first aspect, the optical diffusion element is formed such that a central axis of a luminous flux irradiated toward the irradiated surface is at an angle in a range of 45° to 75° with respect to an optical axis of the image-capturing optical system.

According to an eighth aspect of the present invention, in the multi-spectrum image capturing device according to the seventh aspect, the optical diffusion element includes an optical sheet for diffusing transmittal lights, the optical sheet being disposed in an optical path.

According to a ninth aspect of the present invention, in the multi-spectrum image capturing device according to the seventh aspect, the optical diffusion element includes an optical sheet having a gradation adapted to reduce unevenness in illumination on the irradiated surface, the optical sheet being disposed in an optical path.

According to a tenth aspect of the present invention, in the multi-spectrum image capturing device according to the seventh aspect, the optical diffusion element has a plurality of reflecting surfaces, and at least one of the plurality of reflecting surfaces is an aluminum-coated reflecting surface.

According to an eleventh aspect of the present invention, in the multi-spectrum image capturing device according to the seventh aspect, the optical diffusion element has a plurality of reflecting surfaces, and at least one of the plurality of reflecting surfaces is a white-painted reflecting surface.

According to a twelfth aspect of the present invention, in the multi-spectrum image capturing device according to the seventh aspect, the optical diffusion element has a narrowed portion formed such that a cross-sectional area substantially perpendicular to an optical path for transmitting the lights from the optical rods is smaller in an intermediate region of the optical path than in the entrance side and the exit side of the optical path.

According to a thirteenth aspect of the present invention, there is provided a multi-spectrum image capturing device comprising a multi-spectrum illuminating device for irradiating lights of different wavelengths to an irradiated surface, and an image-capturing optical system for forming an image based on lights reflected from the irradiated surface under illumination by the multi-spectrum illuminating device, components of the reflected lights taken via the image-capturing optical system being analyzed to measure color components of the irradiated surface, wherein the multi-spectrum illuminating device comprises a plurality of light sources for emitting lights of different wavelengths from one another; and a fiber unit constituted by bundling a plurality of optical fibers, the fiber unit being divided in the input light side into a plurality of input light bundles corresponding to the plurality of light sources and being bundled in the output light side into an output light bundle together in a state that the optical fibers constituting the input light bundles are shuffled at random.

According to a fourteenth aspect of the present invention, in the multi-spectrum image capturing device according to the thirteenth aspect, the fiber unit includes an optical sheet for diffusing transmittal lights, the optical sheet being disposed in an optical path.

According to a fifteenth aspect of the present invention, in the multi-spectrum image capturing device according to the thirteenth aspect, the fiber unit includes an optical sheet having a gradation adapted to reduce unevenness in illumination on the irradiated surface, the optical sheet being disposed in an optical path.

According to a sixteenth aspect of the present invention, in the multi-spectrum image capturing device according to the thirteenth aspect, the numbers of the optical fibers assigned to the input light bundles are set depending on emission efficiencies of the corresponding light sources.

According to a seventeenth aspect of the present invention, in the multi-spectrum image capturing device according to the thirteenth aspect, the fiber unit is formed such that a central axis of a luminous flux irradiated toward the irradiated surface is at an angle in a range of 45° to 75° with respect to an optical axis of the image-capturing optical system.

According to an eighteenth aspect of the present invention, in the multi-spectrum image capturing device according to the seventeenth aspect, the fiber unit includes an optical sheet for diffusing transmittal lights, the optical sheet being disposed in an optical path.

According to a nineteenth aspect of the present invention, in the multi-spectrum image capturing device according to the seventeenth aspect, the fiber unit includes an optical sheet having a gradation adapted to reduce unevenness in illumination on the irradiated surface, the optical sheet being disposed in an optical path.

According to a twentieth aspect of the present invention, there is provided a multi-spectrum illuminating device comprising a plurality of light sources for emitting lights of different wavelengths from one another; optical rods for relaying the lights emitted from the light sources; and an optical diffusion element having a reflecting surface to reflect the lights from the optical rods, while diffusing the lights, such that the lights diffused by the reflecting surface are irradiated to the irradiated surface.

According to a twenty-first aspect of the present invention, in the multi-spectrum illuminating device according to the twentieth aspect, the optical diffusion element includes an optical sheet for diffusing transmittal lights, the optical sheet being disposed in an optical path.

According to a twenty-second aspect of the present invention, in the multi-spectrum illuminating device according to the twentieth aspect, the optical diffusion element includes an optical sheet having a gradation adapted to reduce unevenness in illumination on the irradiated surface, the optical sheet being disposed in an optical path.

According to a twenty-third aspect of the present invention, in the multi-spectrum illuminating device according to the twentieth aspect, the optical diffusion element has a plurality of reflecting surfaces, and at least one of the plurality of reflecting surfaces is an aluminum-coated reflecting surface.

According to a twenty-fourth aspect of the present invention, in the multi-spectrum illuminating device according to the twentieth aspect, the optical diffusion element has a plurality of reflecting surfaces, and at least one of the plurality of reflecting surfaces is a white-painted reflecting surface.

According to a twenty-fifth aspect of the present invention, in the multi-spectrum illuminating device according to the twentieth aspect, the optical diffusion element has a narrowed portion formed such that a cross-sectional area substantially perpendicular to an optical path for transmitting the lights from the optical rods is smaller in an intermediate region of the optical path than in the entrance side and the exit side of the optical path.

According to a twenty-sixth aspect of the present invention, there is provided a multi-spectrum illuminating device comprising a plurality of light sources for emitting lights of different wavelengths from one another; and a fiber unit constituted by bundling a plurality of optical fibers, the fiber unit being divided in the input light side into a plurality of input light bundles corresponding to the plurality of light sources and being bundled in the output light side into an output light bundle together in a state that the optical fibers constituting the input light bundles are shuffled at random.

According to a twenty-seventh aspect of the present invention, in the multi-spectrum illuminating device according to the twenty-sixth aspect, the fiber unit includes an optical sheet for diffusing transmittal lights, the optical sheet being disposed in an optical path.

According to a twenty-eighth aspect of the present invention, in the multi-spectrum illuminating device according to the twenty-sixth aspect, the fiber unit includes an optical sheet having a gradation adapted to reduce unevenness in illumination on the irradiated surface, the optical sheet being disposed in an optical path.

According to a twenty-ninth aspect of the present invention, in the multi-spectrum illuminating device according to the twenty-sixth aspect, the numbers of the optical fibers assigned to the input light bundles are set depending on emission efficiencies of the corresponding light sources.

According to a thirtieth aspect of the present invention, in the multi-spectrum illuminating device according to the twenty-sixth aspect, the fiber unit is formed such that a central axis of a luminous flux irradiated toward the irradiated surface is at an angle in a range of 45° to 75° with respect to an optical axis of the image-capturing optical system.

According to a thirty-first aspect of the present invention, in the multi-spectrum illuminating device according to the thirtieth aspect, the fiber unit includes an optical sheet for diffusing transmittal lights, the optical sheet being disposed in an optical path.

According to a thirty-second aspect of the present invention, in the multi-spectrum illuminating device according to the thirtieth aspect, the fiber unit includes an optical sheet having a gradation adapted to reduce unevenness in illumination on the irradiated surface, the optical sheet being disposed in an optical path.

BRIEF DESCRIPTION OF THE DRAWINGS

FIGS. 10A, 10B and 10C are respectively a plan view and a side view showing the configuration of a multi-spectrum illuminating device, which employs fiber bundles for light diffusion, and a view showing exit-side end surfaces of the fiber bundles, according to a third embodiment of the present invention.

DESCRIPTION OF THE PREFERRED EMBODIMENTS

Embodiments of the present invention will be described below with reference to the drawings.

First Embodiment

Figure 1:
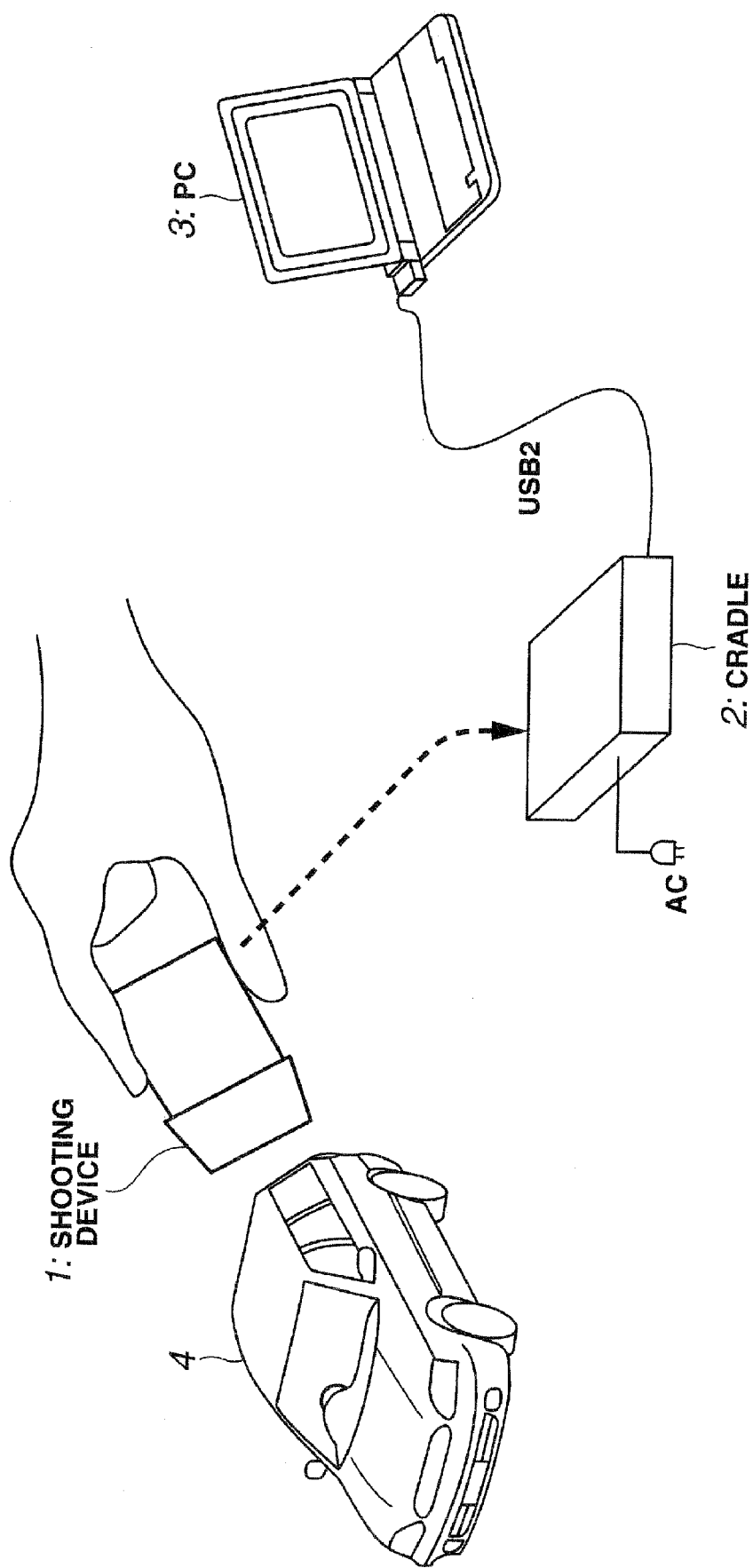
FIG. 1 is an illustration showing the state in use of a multi-spectrum image capturing device according to a first embodiment of the present invention.
Figure 2:
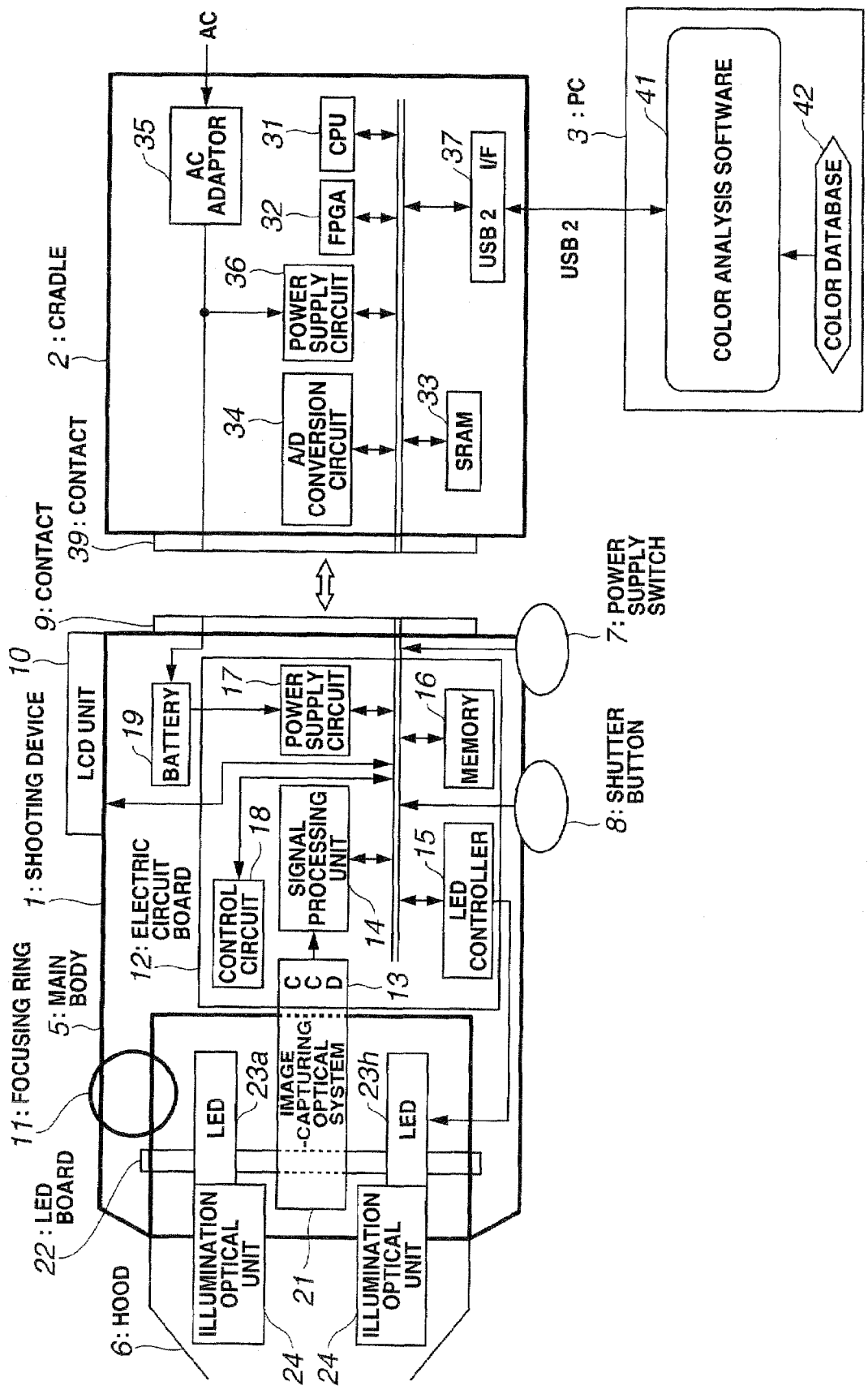
FIG. 2 is a block diagram showing the configuration of the multi-spectrum image capturing device according to the first embodiment.
Figure 5:
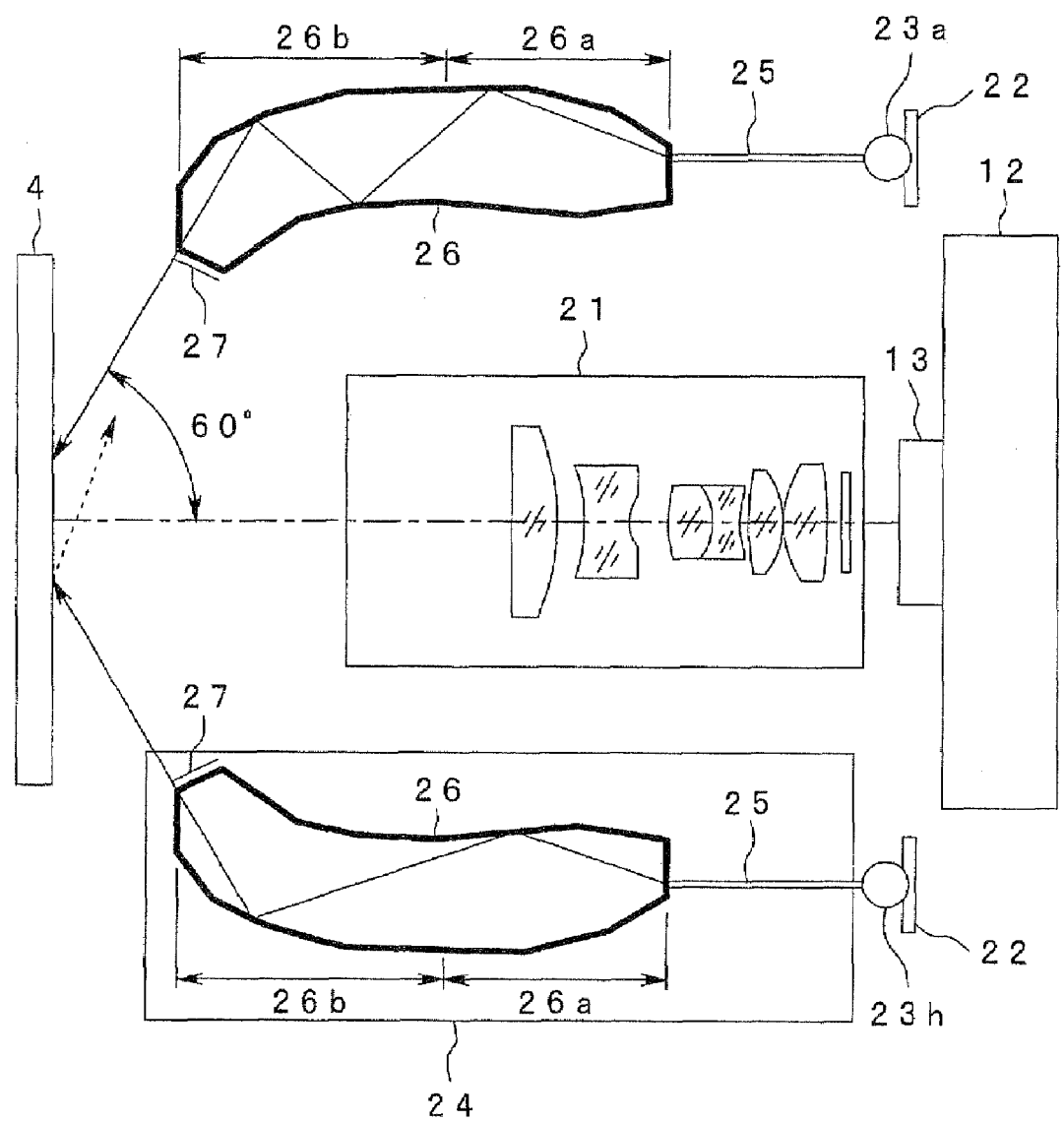
FIG. 5 is a plan view showing the configuration of the multi-spectrum illuminating device according to the first embodiment.
Figure 6:
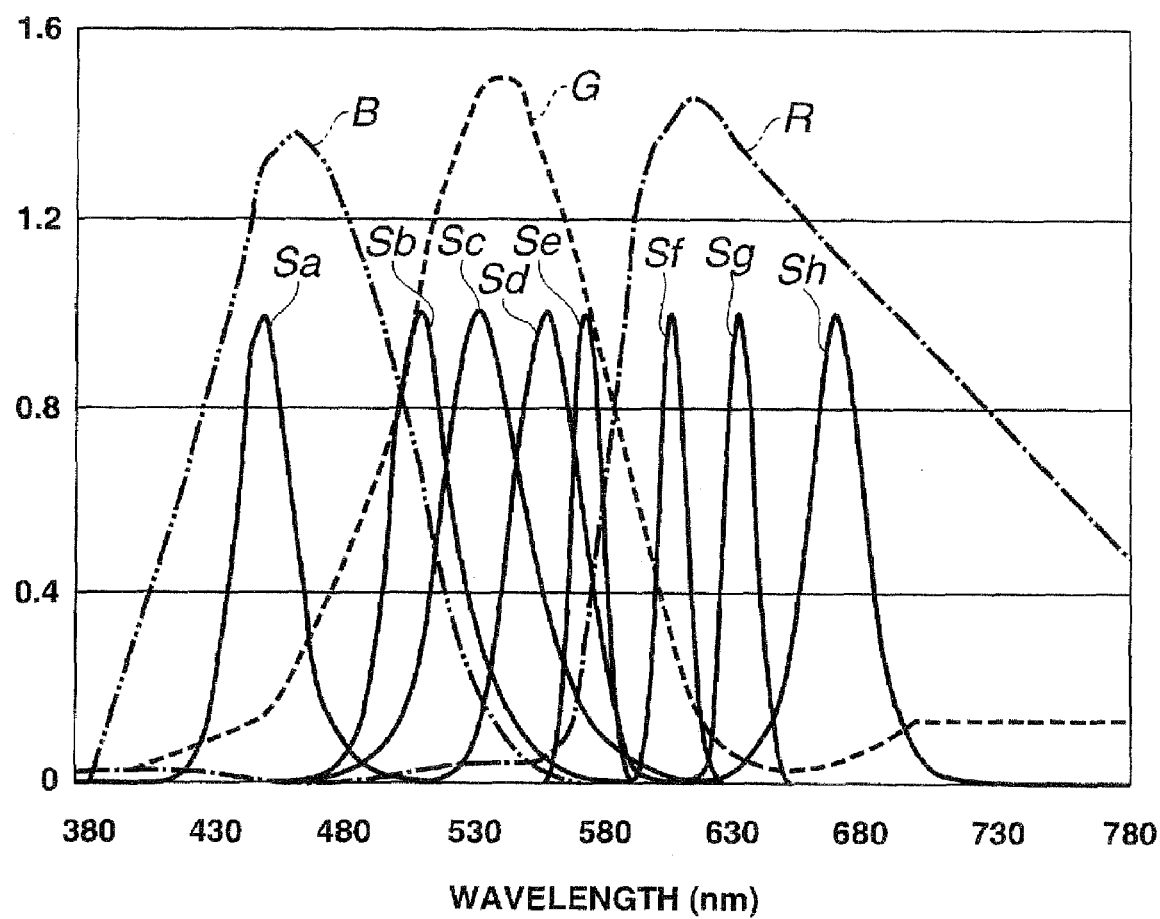
FIG. 6 is a graph showing illumination spectra of LED's and spectral sensitivity of a CCD in the first embodiment.
Figure 7:
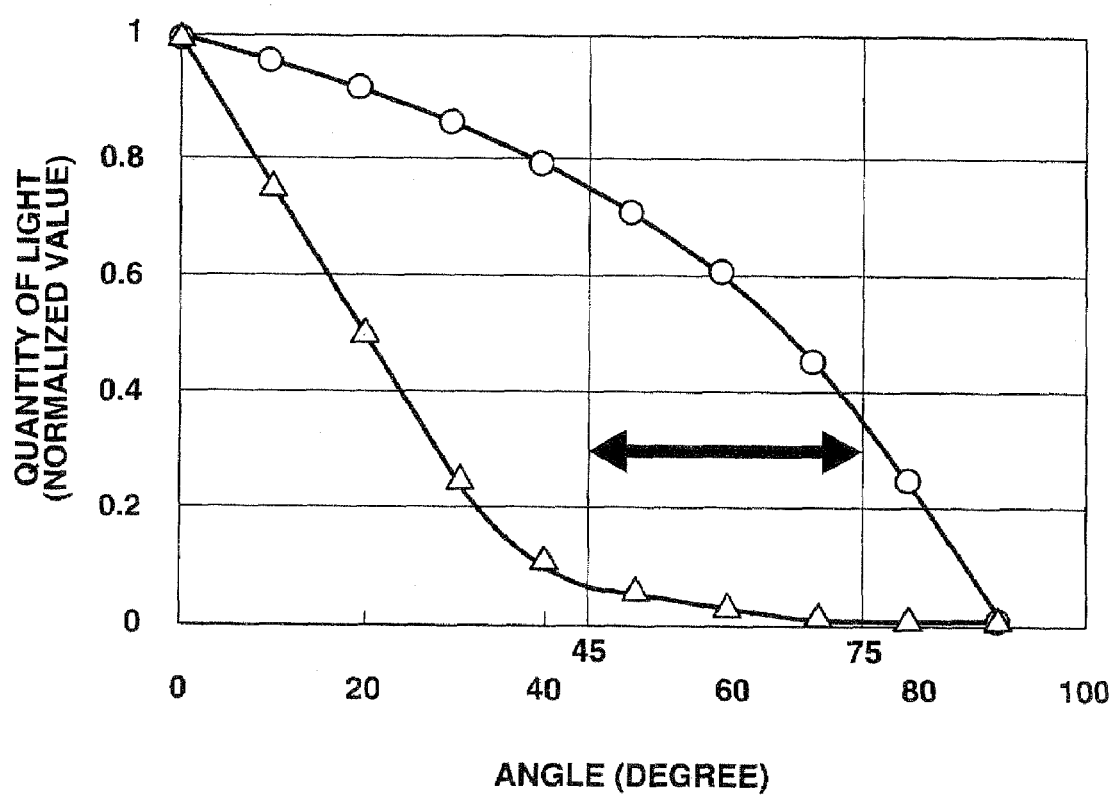
FIG. 7 is a graph showing the correlation of an irradiation angle versus the quantity of regular reflection light and the quantity of color-component reflected light in the first embodiment.

FIGS. 1 through 7 show a first embodiment of the present invention. More specifically, FIG. 1 is an illustration showing the state in use of a multi-spectrum image capturing device; FIG. 2 is a block diagram showing the configuration of the multi-spectrum image capturing device; FIGS. 3A and 3B are respectively a view showing, as viewed from a side, the configuration of the image capturing device, primarily a multi-spectrum illuminating device, and a front view showing the configuration of an LED board; FIGS. 4A and 4B are respectively a perspective view showing the configuration of the multi-spectrum illuminating device and a side view showing the action of an optical sheet; FIG. 5 is a plan view showing the configuration of the multi-spectrum illuminating device; FIG. 6 is a graph showing illumination spectra of LED's and spectral sensitivity of a CCD; and FIG. 7 is a graph showing the correlation of an irradiation angle versus the quantity of regular reflection light and the quantity of color-component reflected light in the first embodiment.

The multi-spectrum image capturing device including the multi-spectrum illuminating device, according to the first embodiment, is employed in applications such as exactly measuring the color of an automobile as a target.

As shown in FIG. 1, a system of the multi-spectrum image capturing device comprises a shooting device 1 for shooting a target 4 such as an automobile, a cradle 2 which is electrically connected to the shooting device 1 when the shooting device 1 is rested on the cradle 2 after the shooting, for example, to perform the functions of, e.g., receiving shot data and charging the shooting device 1 with electricity, and a personal computer (hereinafter abbreviated to as a "PC") 3 which is connected to the cradle 2 and takes in the received shot data from the cradle 2 to perform an analysis.

After shooting the surface of, e.g., an automobile by the shooting device 1 of the multi-spectrum image capturing device, the shooting device 1 is connected to the cradle 2, whereupon the shot data is taken into the PC 3. Then, the PC 3 performs an analysis to discern, for example, whether the color of the automobile is one painted with a proper paint or one painted with other paint. As a result, it is possible to determine the condition of the automobile without expert knowledge regarding the automobile painting.

The configuration of the multi-spectrum image capturing device will be described below with reference to FIG. 2.

The shooting device 1 is constituted of a main body 5 and a hood 6 extending from the main body 5. On an outer surface of the body 5, there are disposed a power supply switch 7 for turning on a power supply of the shooting device 1, a shutter button 8 for inputting an instruction to start the shooting operation, a contact 9 for electrically connecting the shooting device 1 to the cradle 2, an LCD unit 10 for confirming a shot image and displaying various items of information regarding the shooting device 1, and a focusing ring 11 for manually adjusting the focus position of an image-capturing optical system 21 described later.

In an inner space ranging from the hood 6 to the main body 5, the following components are disposed, i.e., LED's 23a-23h serving as light sources for illuminating the target 4, an LED board 22 on which the LED's 23a-23h are mounted, an illumination optical unit 24 for irradiating illumination lights emitted from the LED's 23a-23h, as even illumination lights, to the target 4, and the image-capturing optical system 21 for forming an image based on the lights reflected from an irradiated surface of the target 4 under the illumination on a later-described CCD 13.

In the configuration described above, the multi-spectrum illuminating device is constituted of the LED board 22, the LED's 23a-23h, and the illumination optical unit 24. The image-capturing optical system 21 is constructed as an optical system capable of capturing an image from close range. The hood 6 serves as a light shield to permit entering the image-capturing optical system 21 only by those ones reflected from the target 4 illuminated with the illumination lights, which have been illuminated from the LED's 23a-23h and the illumination optical unit 24, and to protect the incident lights from being affected by other extraneous light. The focusing ring 11 is used to make adjustment such that the image-forming position of an optical image of the target 4 is adjusted by the image-capturing optical system 21 so as to match to an image-capturing surface of the CCD 13. The focusing ring 11 is used in the first embodiment to adjust the focus, but an autofocus mechanism or the like may also be of course used to perform autofocus adjustment.

The main body 5 further incorporates therein the CCD 13 having an RGB color filter and converting an optical target image formed by the image-capturing optical system 21 to an electric image signal, a signal processing circuit 14 for executing various kinds of signal processing on an image signal outputted from the CCD 13, an LED controller 15 for controlling the LED's 23a-23h to emit respective lights, a memory 16 for storing image data processed by the signal processing circuit 14, processing programs and data, etc. executed by a later-described control circuit 18, a battery 19 for accumulating electric power supplied from the cradle 2 through the contact 9, a power supply circuit 17 for supplying the electric power supplied from the battery 19 to various circuits in the shooting device 1, an electric circuit board 12 on which the CCD 13, the signal processing circuit 14, the LED controller 15, the memory 16, the power supply circuit 17 and the control circuit 18 are mounted, and the control circuit 18 connected to each of the LCD unit 10, the signal processing circuit 14, the LED controller 15, the memory 16 and the power supply circuit 17 for two-way communication via a bus, etc. and controlling the whole of the shooting device 1 including those components in a supervisory manner.

The cradle 2 includes a contact 39 for connection to the contact 9 of the shooting device 1, an AC adaptor 35 for converting an AC current at a predetermined voltage, which is supplied from an AC power supply, to a DC voltage as required, a power supply circuit 36 for supplying electric power supplied from the AC adaptor 35 to various circuits in the cradle 2, an A/D conversion circuit 34 for converting the image data transmitted from the shooting device 1 to digital data when the former is analog data, an SRAM 33 for storing the image data, processing programs and data, etc. executed by a later-described CPU 31, an FPGA (Field Programmable Gate Array) 32 for executing, e.g., compression of the image data, a USB2I/F 37 serving as an interface for communicating with the PC 3 via USB2, for example, and the CPU 31 connected to each of the FPGA 32, the SRAM 33, the A/D conversion circuit 34, the power supply circuit 36 and the USB2I/F 37 for two-way communication via a bus, etc., controlling the whole of the cradle 2 including those components in a supervisory manner, and controlling the communication with the shooting device 1 and the PC 3.

Color analysis software 41 is installed in the PC 3, the color analysis software 41 analyzing the image data received from the shooting device 1 through the cradle 2 connected to the PC 3 via USB2, for example, thereby determining the color of the target 4, and also a color database 42 is stored in the PC 3, the color database 42 being referred to when the color analysis software 41 executes the color analysis.

The illumination optical unit and the LED's will be described below with reference to FIGS. 3A through 7.

Figure 3A:
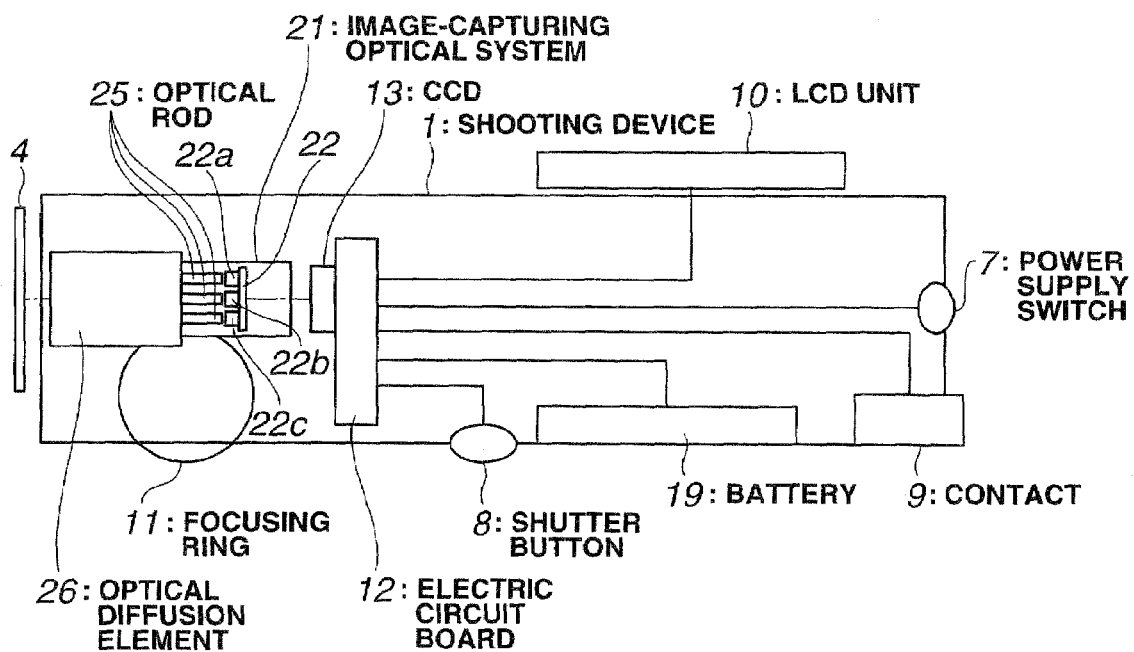
FIGS. 3A and 3B are respectively a view showing, as viewed from a side, the configuration of a shooting device, primarily a multi-spectrum illuminating device, and a front view showing the configuration of an LED board, according to the first embodiment.
Figure 3B:
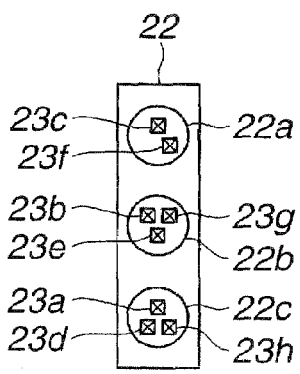
Figure 4:
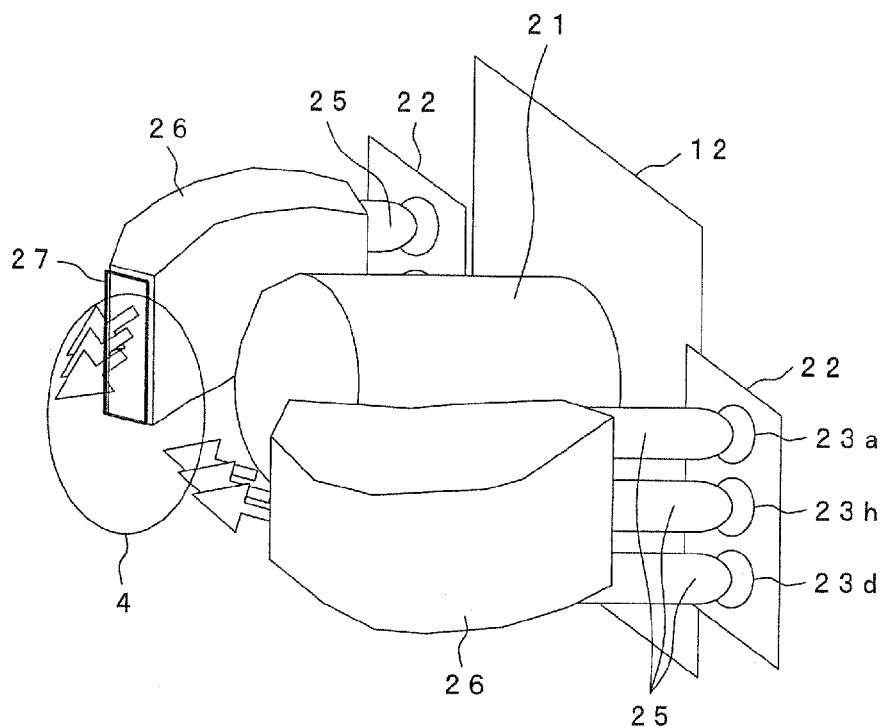
FIGS. 4A and 4B are respectively a perspective view showing the configuration of the multi-spectrum illuminating device and a side view showing the action of an optical sheet, according to the first embodiment.
Figure 4:
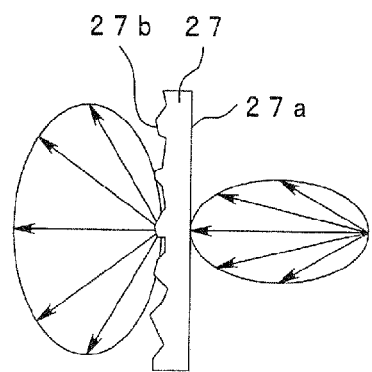

As shown in FIG. 3B, the LED's 23a-23h mounted on the LED board 22 are packaged in separate groups, i.e., in a plurality of light emitting units. For example, the LED's 23c and 23f are packaged in a first light emitting unit 22a, the LED's 23b, 23e and 23g are packaged in a second light emitting unit 22b, and the LED's 23a, 23d and 23h are packaged in a third light emitting unit 22c, respectively. While the first embodiment is described as using an example in which each eight LED's which emit lights of eight different wavelength ranges in provided, a plurality of LED's may be provided corresponding to the light of one wavelength range.

The LED's 23a-23h have emission spectra as shown in FIG. 6. The LED 23a has a central emission wavelength of 450 nm as indicated by a curve Sa. The LED 23b has a central emission wavelength of 505 nm as indicated by a curve Sb. The LED 23c has a central emission wavelength of 525 nm as indicated by a curve Sc. The LED 23d has a central emission wavelength of 560 nm as indicated by a curve Sd. The LED 23e has a central emission wavelength of 575 nm as indicated by a curve Se. The LED 23f has a central emission wavelength of 609 nm as indicated by a curve Sf. The LED 23g has a central emission wavelength of 635 nm as indicated by a curve Sg. The LED 23h has a central emission wavelength of 670 nm as indicated by a curve Sh.

Corresponding to those emission spectra, the CCD 13 including the RGB color filter has spectral sensitivity for each filter color, as shown in FIG. 6, such that respective sensitivity curves are not completely separated, but they are partly overlapped with each other. More specifically, the spectral sensitivity through a B-color filter covers, as indicated by a curve B, almost the whole of the emission band of the LED 23a and a part of the emission band of the LED 23b. The spectral sensitivity through a G-color filter covers, as indicated by a curve G, almost the whole of the emission bands of the LED 23b, the LED 23c, the LED 23d and the LED 23e. Further, the spectral sensitivity through an R-color filter covers, as indicated by a curve R, almost the whole of the emission bands of the LED 23f, the LED 23g and the LED 23h.

As shown in FIG. 3A, the illumination optical unit 24 includes a plurality of optical rods 25 for transmitting the illumination lights emitted from the LED's 23a-23h, and an optical diffusion element 26 for diffusing the illumination lights transmitted through the optical rods 25 so as to make even illumination lights. Further, the optical diffusion element 26 includes, as shown in FIGS. 4A, 4B and 5, an optical sheet 27 disposed in the exit-end surface side for further diffusing the illumination lights.

The optical rods 25 can be constituted of suitable one of various forms. As a typical example, the optical rods 25 are formed as a single rod-like member made of an optical material or as a fiber bundle.

The optical diffusion element 26 is formed such that it has a substantially rectangular shape as shown in FIG. 3A when viewed from a side, but has a curved shape as shown in FIG. 5 when viewed from above (or as shown in FIG. 4A when viewed in perspective). The optical diffusion element 26 thus formed reflects the lights transmitted through the optical rods 25 plural times by its inner surface for diffusion of the lights.

As shown in FIG. 5, the entrance side of the optical diffusion element 26, upon which the lights from the optical rods 25 are incident, is constituted as a white diffusion surface 26a, and the exit side from which the lights emerge is constituted as an aluminum-coated reflecting surface 26b. With such an arrangement, the optical diffusion element 26 is able to transmit the illumination lights toward the exit end side, while evenly diffusing the illumination lights, without reducing the light quantity.

Further, as shown in FIG. 5, the optical diffusion element 26 is arranged such that a central axis of a luminous flux irradiated toward an irradiated surface is at an angle of about 60° with respect to an optical axis of the image-capturing optical system 21. That arrangement is based on design aiming to efficiently take in the color-component reflected light while suppressing the influence of the regular reflection light.

More specifically, as indicated by triangular marks in FIG. 7, when the central axis of the irradiation luminous flux is at the angle of 0° with respect to the image-capturing optical axis, the quantity of the regular reflection light is maximized. As that angle increases, the quantity of the regular reflection light is reduced to such an extent that the influence of the regular reflection light is practically insignificant when the angle exceeds about 45°. On the other hand, as indicated by circular marks in FIG. 7, the quantity of the color-component reflected light is also maximized when the above-mentioned angle is 0°, and is reduced as that angle increases. However, the quantity of the color-component reflected light is attenuated more moderately than the quantity of the regular reflection light, and therefore the difference between the quantities of those reflected lights is increased; namely, an SN ratio is improved. Even at 45° where the influence of the regular reflection light becomes practically insignificant, the quantity of the color-Component reflected light still remains at a practically useful level. Thereafter, when the above-mentioned angle is further increased to reach about 75°, the quantity of the color-component reflected light is reduced to a not-negligible extent and departs from a practically usable range. Accordingly, the practically usable range where the SN ratio is high and the quantity of the color-component reflected light is obtained at a required level is given by a range of the above-mentioned angle from 45° to 75°. In the first embodiment, the angle of about 60° is set as an optimum value within the practically usable range at which maximum efficiency is obtained and the color measurement can be performed with maximum accuracy.

As shown in FIG. 4B, the optical sheet 27 has an entrance surface 27a being flat and an exit surface 27b serving as a diffusion surface. The illumination lights made even by the optical diffusion element 26 are further diffused by the optical sheet 27 to become more even lights, which are irradiated to the target 4.

The operation of the multi-spectrum image capturing device thus constructed will be described below.

A user holds the shooting device 1 with the hood 6 directed toward an area to be shot of the target 4, and operates the power supply switch 7 to turn on the power for the shooting device 1. Responsively, the various circuits on the electric circuit board 12 are supplied with the electric power from the battery 19 to start the operations.

Upon start of the operation in accordance with a control program, the control circuit 18 executes predetermined initialization, etc. and performs control, via the LED controller 15, to supply a current to the LED board 22. The LED's 23a-23h mounted on the LED board 22 are thereby all turned on at the same time, for example. While, in such a manner, all the LED's 23a-23h can be turned on at the same time, it is also possible to turn on any desired one or desired two or more of the LED's 23a-23h. For example, the turning-on of all the LED's 23a-23h is made in the case of observing the target 4 via the LCD unit 10, and the turning-on of individual one of the LED's 23a-23h is made in the case of measuring the color of the target 4. Also, a value of the current supplied to the LED's 23a-23h is changeable. In particular, when the target is observed via the LCD unit 10, the current value is preferably changed to control the light quantity such that the target 4 can be observed under proper illuminance while power consumption is reduced.

With the electric power supplied to the LED's 23a-23h in that way, the LED's 23a-23h emit lights of respective wavelengths at predetermined emission angles. Those lights are irradiated as the illumination lights to the target 4 through the illumination optical unit 24.

While observing the shot area of the target 4 via a screen of the LCD unit 10, the user operates the focusing ring 11 such that the shot area is focused. In the focused state, the user depresses the shutter button 8, thus starting the operation of taking in an image for the color measurement of the shot area.

More specifically, upon detecting the depression of the shutter button 8, the control circuit 18 instructs the LED controller 15 to perform the emission operation in a measurement mode. In response to the instruction, the LED controller 15 operates the eight LED's 23a-23h, which are mounted on the LED board 22 and supplied with the current, to sequentially repeat turning-on/off at intervals of 1/30 sec. Because the LED's 23a-23h have different emission efficiencies depending on wavelengths as shown in FIG. 6, the LED controller 15 causes each of the LED's 23a-23h to emit the light in quantity required for the shooting while controlling a value of the supplied current.

The light emitted from each of the LED's 23a-23h at the predetermined angle enters the corresponding optical rod 25 and is transmitted to the optical diffusion element 26. After entering the optical diffusion element 26, the light is first reflected by the white diffusion surface 26a. The optical diffusion element 26 is formed as, e.g., a box-like element having an inner cavity, and the white diffusion surface 26a is formed by coating, on an inner surface of the box-like element, fine white paint particles capable of diffusively reflecting the lights of all wavelengths at a reflectance which is not depending on the wavelength. The diffusion of the transmittal light is positively promoted by the reflecting action of the white diffusion surface 26a.

After the action of promoting the diffusion is repeated by the white diffusion surface 26a plural times in such a manner, the aluminum-coated reflecting surface 26b reflects the light without substantially reducing the light quantity. As a result, at a stage where the lights emerge from the optical diffusion element 26, the light is obtained in a state close to integrated light.

The emergent light is further diffused by the first optical sheet 27 to become the illumination light made more even with respect to the irradiated surface, which is then irradiated to the target 4. At this time, because extraneous light is shielded by the hood 6, the target 4 is illuminated substantially only by the illumination light from the LED.

The irradiated light is reflected by the target 4 and enters the image-capturing optical system 21 where an image based on the light is formed on the image-capturing surface of the CCD 13. The light entering the image-capturing optical system 21 at that time is substantially only the color-component reflected light and not-appreciably contains the regular reflection light for the reason described above.

The image data produced with photoelectric conversion in the CCD 13 is subjected to signal processing in the signal processing circuit 14 and is accumulated in the memory 16.

The above-described operation is executed corresponding to the sequential turning-on/off of the LED's 23a-23h, and the image data corresponding to eight different wavelengths are sequentially accumulated in the memory 16. Such a process of taking in eight sets of the image data may be executed only once, but it is also possible to repeat the process plural times for increasing reliability of the data.

After the measuring operation using the shooting device 1 is completed, the user rests the shooting device 1 on the cradle 2 such that electrical connection is established between the contacts 9 and 39.

Correspondingly, the control circuit 18 in the shooting device 1 and the CPU 31 in the cradle 2 start communication to transfer the image data stored in the memory 16 from the shooting device 1 to the cradle 2.

After temporarily accumulating the received image data in the SRAM 33, the cradle 2 processes the image data by the FPGA 32 and transmits the processed data to the PC 3 via the USB2I/F 37.

The PC 3 analyzes the received image data by the color analysis software 41 installed therein. The analysis is executed while referring to the color database 42 stored in the PC 3. The exact color of the subject is definitely analyzed by the PC 3, and the analyzed result is displayed on, e.g., a monitor of the PC 3.

Also, with the connection of the shooting device 1 to the cradle 2, the battery 19 in the shooting device 1 is supplied with the electric power from the AC adaptor 35 in the cradle 2 via the contacts 9 and 39 and is charged.

According to the first embodiment described above, since the multi-spectrum illuminating device includes the optical diffusion element, the light emitted from the LED can be irradiated as the even illumination light. Also, since the light emitted from the LED is transmitted to the optical diffusion element through the optical rod, the light can be effectively transmitted without causing a loss of the light. Further, since the optical diffusion element includes the white diffusion surface, the illumination light can be efficiently made even. In addition, since the optical sheet having the function of diffusing the light is disposed at the exit surface of the optical diffusion element, the illumination light can be made more even. Still further, since the central axis of a luminous flux of the illumination light is set at an angle of about 60°, in particular, within the range of 45° to 75°, with respect to the image-capturing optical axis, the color-component reflected light can be efficiently captured without being substantially affected by the regular reflection light. As a result, exact color measurement can be realized.

Second Embodiment

Figure 8A:
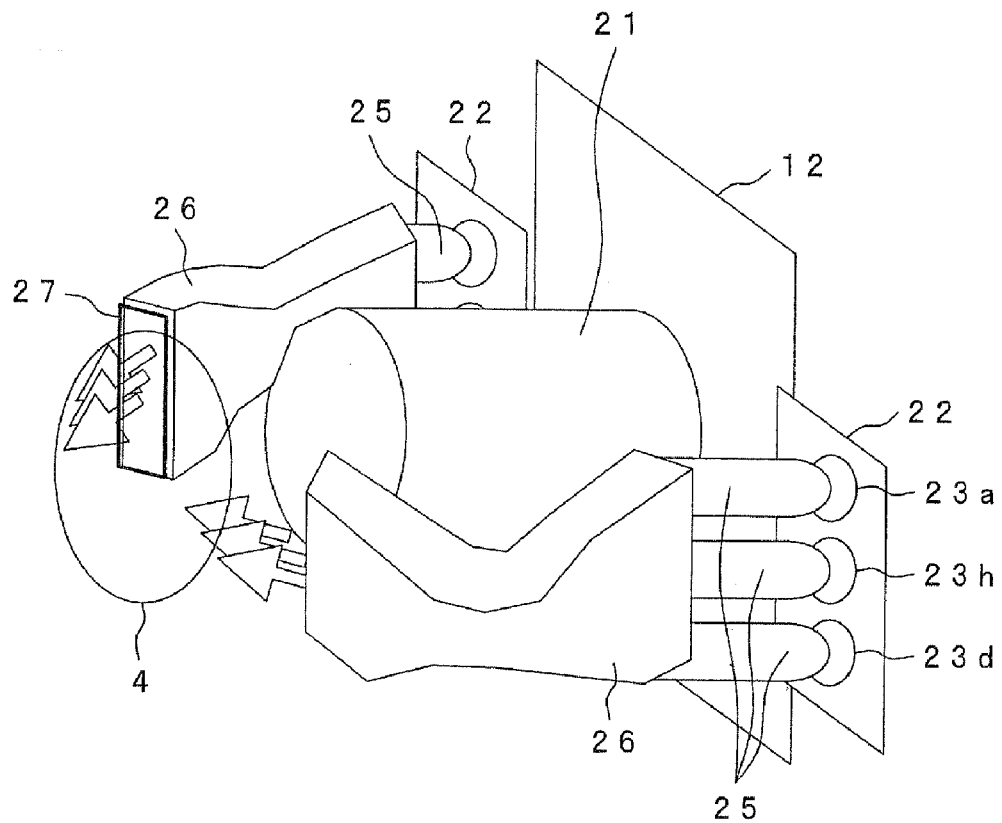
FIGS. 8A and 8B are respectively a perspective view showing a multi-spectrum illuminating device provided with an optical diffusion element having a diaphragm structure and a view showing, as viewed from a side, how lights are reflected by the optical diffusion element, according to a second embodiment of the present invention.
Figure 8B:
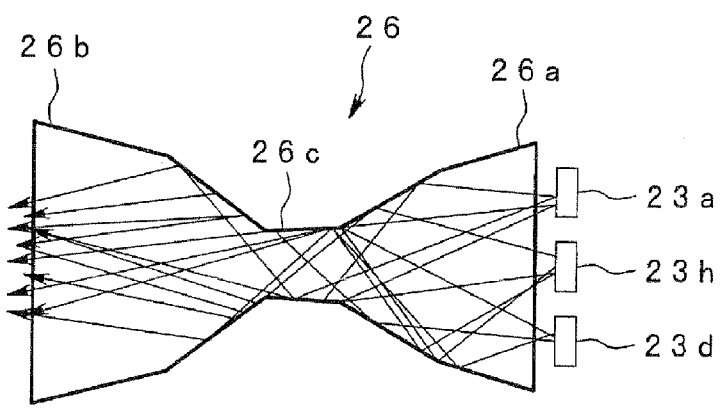
Figure 9A:
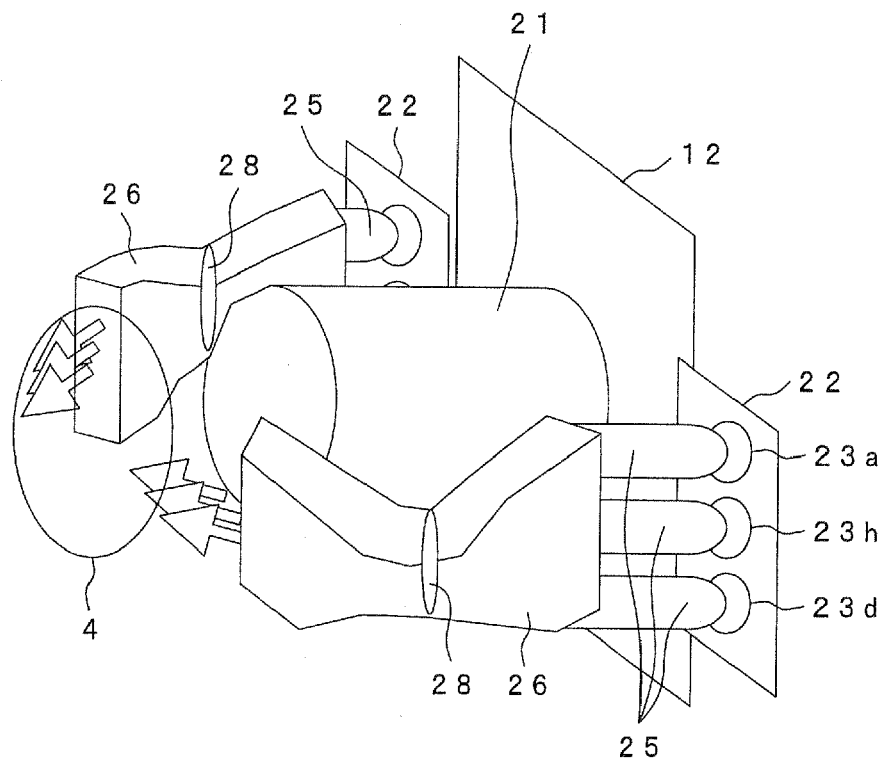
FIGS. 9A and 9B are respectively a perspective view showing the multi-spectrum illuminating device provided with the optical diffusion element having the diaphragm structure, which element includes an optical sheet in the diaphragm structure, and a view showing, as viewed from a side, how lights are reflected by the optical diffusion element, according to the second embodiment of the present invention.
Figure 9B:
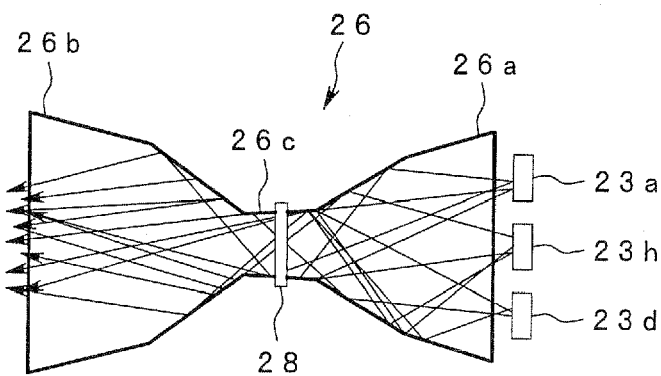

FIGS. 8A, 8B, 9A and 9B show a second embodiment of the present invention. More specifically, FIGS. 8A and 8B are respectively a perspective view showing a multi-spectrum illuminating device provided with an optical diffusion element having a diaphragm structure and a view showing, as viewed from a side, how lights are reflected by the optical diffusion element. FIGS. 9A and 9B are respectively a perspective view showing the multi-spectrum illuminating device provided with the optical diffusion element having the diaphragm structure, and including an optical sheet in the diaphragm structure part, and a view showing, as viewed from a side, how lights are reflected by the optical diffusion element.

Similar components in the second embodiment to those in the first embodiment are denoted by the same numerals and a description of those components is omitted here. The following description is made primarily for different points.

In the second embodiment, the optical diffusion element 26 is formed to have a different shape from that in the first embodiment. The optical diffusion element 26 in the second embodiment has substantially the same shape as that in the first embodiment, shown in FIG. 5, when viewed from above, but it has a shape narrowed in a central portion as shown in FIG. 8B when viewed from a side (or as shown in FIG. 8A when viewed in perspective).

More specifically, the optical diffusion element 26 has a narrowed portion 26c formed in an intermediate region of an optical path for transmission of the lights through it, the region being between a white diffusion surface 26a in the entrance side upon which the lights are incident and an aluminum-coated reflecting surface 26b in the exit side from which the lights emerge. The narrowed portion 26c is formed in such a narrowed shape that a cross-sectional area substantially perpendicular to the optical path for transmission of the lights is smaller than the cross-sectional area of an entrance-side end surface of the optical diffusion element 26 upon which the lights from the optical rods 25 are incident, and is also smaller than the cross-sectional area of an exit-side end surface thereof from which the lights are irradiated toward the optical sheet 27.

When the lights emitted from the LED's 23a-23h enter the thus-formed optical diffusion element 26 via the optical rods 25, each luminous flux of the lights is gradually converged toward the narrowed portion 26c while being reflected plural times by the white diffusion surface 26a in the entrance side. During such a luminous flux converging process, diffusion of the light is promoted. Then, the luminous flux is diverged starting from the narrowed portion 26c and is reflected by the aluminum-coated reflecting surface 26b. As shown in FIG. 8B, the aluminum-coated reflecting surface 26b is formed into a shape analogous to, e.g., a paraboloid. In a similar manner to the case where light irradiated from a focus of the paraboloid is reflected to become light parallel to a symmetric axis of the paraboloid, the light beams reflected by the aluminum-coated reflecting surface 26b become light beams substantially parallel to each other. Thus, the even and substantially parallel luminous flux emerges from the optical diffusion element 26.

The lights emerging from the optical diffusion element 26 are further diffused by the optical sheet 27 and then irradiated to the target 4 as in the first embodiment.

FIGS. 9A and 9B show an example in which an optical sheet 28 having the light diffusion function is disposed inside the optical diffusion element 26 shaped as shown in FIGS. 8A and 8B. While the optical sheet 27 is disposed in the exit surface side of the optical diffusion element 26 in the example shown in FIGS. 8A and 8B, the optical sheet 28 is disposed inside the optical diffusion element 26 in the example shown in FIGS. 9A and 9B. More specifically, the optical sheet 28 is disposed in the narrowed portion 26c, i.e., in the position where the luminous flux is maximally converged in the optical diffusion element 26.

With such an arrangement, the light diffusion is more effectively performed in the position of the narrowed portion 26c. The lights diffused by the optical sheet 28 are reflected by the aluminum-coated reflecting surface 26b and emerge as substantially parallel lights from the optical diffusion element 26 in a similar manner to that in the foregoing example.

In addition to substantially the same advantages as those obtained with the first embodiment, the second embodiment can provide the advantages as follows. With the provision of the narrowed portion, the luminous flux is each reflected in larger number of times during the process in which the luminous flux is converged and then diverged, and therefore more even illumination lights can be obtained. On the other hand, when the illumination lights are required to have evenness comparable to that in the first embodiment, the overall length of the optical diffusion element can be reduced and the element size can be cut. It is hence possible to provide a smaller-sized multi-spectrum illuminating device and a smaller-sized multi-spectrum image capturing device.

Further, in the case of the optical sheet being disposed in the narrowed portion, since the presence of the optical sheet does not prevent the lights irradiated to the target from becoming the substantially parallel lights, the quantity of light uselessly leaking to the hood side can be reduced and the target can be more efficiently illuminated under higher illuminance. On the other hand, when the needed illuminance is comparable to that in the first embodiment, the electric power supplied to the LED's can be reduced. It is hence possible to provide a multi-spectrum image capturing device consuming less power and having a longer service time.

Third Embodiment

FIGS. 10A, 10B and 10C and FIGS. 11A, 11B, 11C, 11D and 11E show a third embodiment of the present invention. More specifically, FIGS. 10A, 10B and 10C are respectively a plan view and a side view showing the configuration of a multi-spectrum illuminating device, which employs fiber bundles for light diffusion, and a view showing exit-side end surfaces of the fiber bundles. FIGS. 11A, 11B, 11C, 11D and 11E are illustrations and graphs for explaining correction of unevenness in illumination with an optical sheet resulted by obliquely irradiating lights obliquely.

Similar components in the third embodiment to those in the first and second embodiments are denoted by the same numerals and a description of those components is omitted here. The following description is made primarily for different points.

The multi-spectrum illuminating device of the third embodiment comprises the LED board 22, the LED's 23a-23h mounted on the LED board 22, fiber bundles 52 for transmitting the lights emitted from the LED's 23a-23h while making the lights even, the fiber bundles 52 constituting a fiber unit, and a second optical sheet 54 for correcting illumination unevenness caused by obliquely irradiating the lights from the fiber bundles 52 toward the target 4, the second optical sheet 54 constituting the fiber unit.

Each of the fiber bundles 52 is formed by bundling a plurality of very thin single fibers (optical fibers) with a size of about 50 μm, for example. The fiber bundles 52 are constituted at one end side as input light bundles 51a-51h to receive respective lights emitted from the LED's 23a-23h at predetermined exit angles, and at the other end side as an output light bundle 53 for irradiating the lights toward the target 4.

The optical fibers bundled into eight divided groups at the input light bundles 51a-51h are shuffled one another at random in the course of an optical path for transmission of the lights through it, and are bundled again into the output light bundle 53 as indicated by an arrow A in FIG. 10C.

On that occasion, the number of the optical fibers bundled to each of the input light bundles 51a-51h is assigned with such a value as providing the quantity of light, which is required for the exiting light, depending on the emission efficiency of each of the LED's 23a-23h. Assuming the LED's 23a, 23h and 23d, shown in FIG. 10B, to have emission efficiencies at a ratio of 1:1.5:2, for example, the optical fibers are bundled such that the numbers of the optical fibers bundled to the input light bundles 51a, 51h and 51d corresponding to the LED's 23a, 23h and 23d are set to a ratio of 1:0.67:0.5.

With such an arrangement, the lights taken in from the input light bundles 51*a*-51*h* in respective proper quantities are shuffled at random and then emerge, as evenly distributed illumination lights, from the output light bundle 53 as shown in FIG. 10C.

Figure 11A:
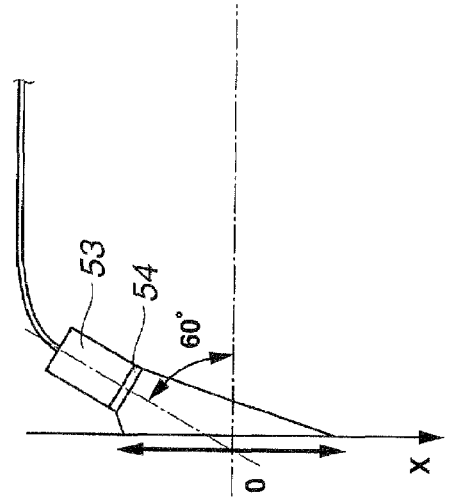
FIGS. 11A, 11B, 11C, 11D and 11E are illustrations and graphs for explaining correction of unevenness in illumination by using an optical sheet and by obliquely irradiating lights, in the third embodiment.
Figure 11B:
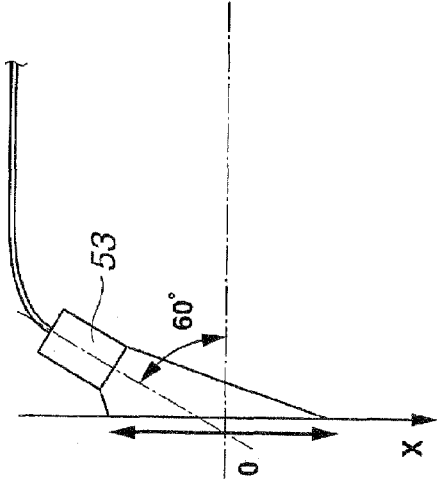

In addition, as shown in FIGS. 10A, 11A and 11B, the output light bundle 53 is arranged such that the central axis of the luminous flux irradiated toward the irradiated surface is at an angle of about 60° with respect to the optical axis of the image-capturing optical system 21. The reason is the same as that described above in connection with the first embodiment. Namely, that arrangement aims to efficiently take in the color-component reflected light while suppressing the influence of the regular reflection light.

Figure 11C:
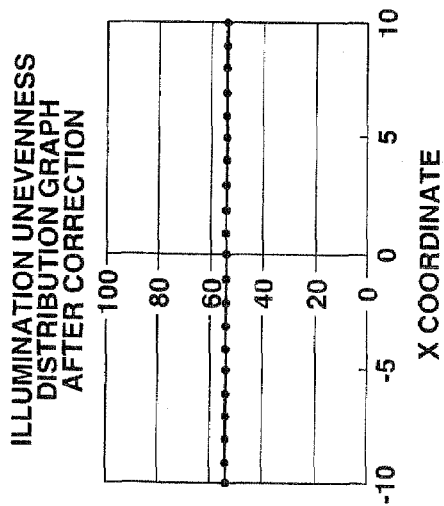

The lights emerging from the output light bundle 53 at such an angle may cause, for example, illumination unevenness shown in FIG. 11C, on the irradiated surface of the target 4. The second optical sheet 54 is provided to correct that illumination unevenness.

Figure 11D:
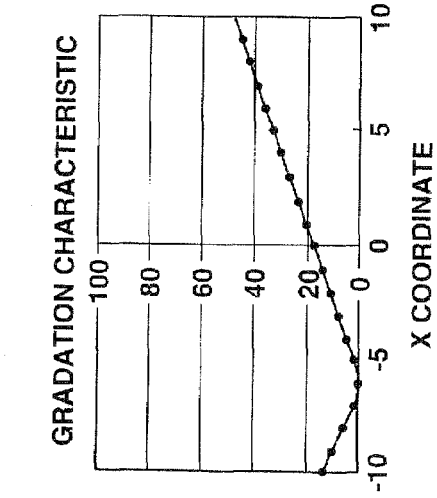

The optical sheet 54 has a gradation characteristic shown in FIG. 11D, and a characteristic curve has a shape inverting the shape of a luminance distribution representing the illumination unevenness.

Figure 11E:
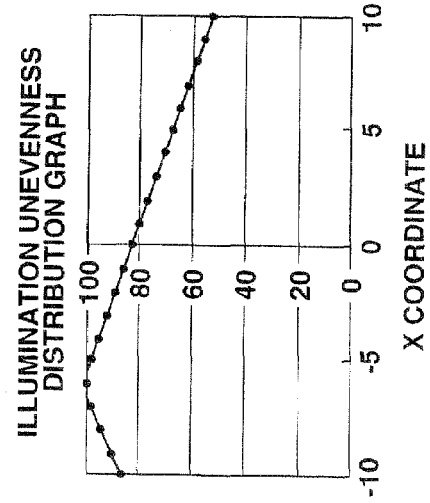

The illumination lights from the output light bundle 53 pass via the optical sheet 54 having the gradation characteristic and are irradiated to the irradiated surface of the target 4 at the illuminance shown in FIG. 11E. As a result, the illumination not including illumination unevenness is realized.

The optical sheet used in the above-described first and second embodiments for diffusing the transmittal lights may be additionally disposed in optical paths of the fiber bundles. The third modification enables the lights to be irradiated in a more evenly diffused state.

According to the third embodiment described above, substantially the same advantages as those obtained with the first and second embodiments can also be obtained by using the fiber bundles and shuffling the optical fibers at random in the course of optical path between the entrance side and the exit side.

Further, since the second optical sheet is provided in the exit side surface of the output light bundle, it is possible to satisfactorily correct the illumination unevenness that is caused due to oblique light irradiation, and to obtain even illuminance in the irradiated surface of the target.

The second optical sheet 54 used in the third embodiment can also be disposed in the exit surface side of the optical diffusion element 26 in the first and second embodiments. In that case, the modification can also provide same advantages for the first and second embodiments.

The optical diffusion element 26 used in the first to third embodiments is not limited to one formed by coating white paint particles on the inner surface of the white diffusion surface 26*a*. Instead, the optical diffusion element 26 may be formed of a resin containing a white additive at a predetermined ratio, e.g., a resin containing an additive of which main component is white $TiO_2$ (titanium oxide), at a ratio of smaller than 5%.

In that case, by mixing an additive with high quality (stable and high reflectance at desired wavelengths) in material and forming the optical diffusion element by, e.g., injecting and molding the material, an optical diffusion element having high performance can be easily and inexpensively obtained without requiring secondary treatment, such as painting.

It is to be noted that present invention is not limited to the above-described embodiments and can be practiced in various modifications and applications without departing the gist of the invention.

What is claimed is:

1. A multi-spectrum image capturing device comprising:
   a multi-spectrum illuminating device for irradiating lights of different wavelengths to an irradiated surface; and
   an image-capturing optical system for forming an image based on lights reflected from the irradiated surface under illumination by the multi-spectrum illuminating device;
   wherein components of the reflected lights captured via the image-capturing optical system are analyzed to measure color components of the irradiated surface; and
   wherein the multi-spectrum illuminating device comprises:
      a plurality of light sources for emitting the lights of different wavelengths; and
      a pair of fiber units, each of which comprises a plurality of optical fibers which are divided at a light input side of the fiber unit into a plurality of input light bundles corresponding to a plurality of the light sources, and which are bundled at a light output side of the fiber unit into an output light bundle in which the optical fibers constituting the input light bundles are shuffled at random;
   wherein the pair of the fiber units are provided so as to be opposed to the image-capturing optical system and so as to be separated from each other; and
   wherein each of the pair of the fiber units comprises a first optical sheet, which is disposed on an exit-side surface of the output light bundle and through which the lights are transmitted, and which has a gradation characteristic which is reversed with respect to a luminance distribution of illumination unevenness on the irradiated surface, in order to reduce the illumination unevenness on the irradiated surface.

2. The multi-spectrum image capturing device according to claim 1, wherein the fiber unit further comprises a second optical sheet, which is disposed in an optical path of the lights and through which the lights are transmitted, for diffusing the transmitted lights.

3. The multi-spectrum image capturing device according to claim 1, wherein numbers of the optical fibers assigned to the input light bundles are set depending on emission efficiencies of the corresponding light sources.

4. The multi-spectrum image capturing device according to claim 1, wherein the fiber unit is formed such that a central axis of a luminous flux irradiated toward the irradiated surface is at an angle in a range of 45° to 75° with respect to an optical axis of the image-capturing optical system.

5. The multi-spectrum image capturing device according to claim 4, wherein the fiber unit further comprises a second optical sheet, which is disposed in an optical path of the lights and through which the lights are transmitted, for diffusing the transmitted lights.

6. A multi-spectrum illuminating device comprising:
   a plurality of light sources for emitting lights of different wavelengths; and
   a pair of fiber units, each of which comprises a plurality of optical fibers which are divided at a light input side of the fiber unit into a plurality of input light bundles corresponding to a plurality of the light sources, and which are bundled at a light output side of the fiber unit into an output light bundle in which the optical fibers constituting the input light bundles are shuffled at random;
   wherein the pair of the fiber units are provided so as to be separated from each other; and
   wherein each of the pair of the fiber units comprises a first optical sheet, which is disposed on an exit-side surface of the output light bundle and through which the lights are transmitted, and which has a gradation characteristic which is reversed with respect to a luminance distribution of illumination unevenness on the irradiated surface, in order to reduce the illumination unevenness on an irradiated surface.

7. The multi-spectrum illuminating device according to claim 6, wherein the fiber unit further comprises a second optical sheet, which is disposed in an optical path of the lights and through which the lights are transmitted, for diffusing the transmitted lights.

8. The multi-spectrum illuminating device according to claim 6, wherein numbers of the optical fibers assigned to the input light bundles are set depending on emission efficiencies of the corresponding light sources.

* * * * *